(12) United States Patent
Chen (10) Patent No.: US 9,155,858 B2
(45) Date of Patent: Oct. 13, 2015

(54) LIQUID CONTAINER FOR GAS HUMIDIFICATION AND LIQUID STORAGE DEVICE

(71) Applicant: APEX MEDICAL CORP., New Taipei (TW)

(72) Inventor: Hsin-Hung Chen, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 146 days.

(21) Appl. No.: 13/970,875

(22) Filed: Aug. 20, 2013

(65) Prior Publication Data

US 2015/0054183 A1 Feb. 26, 2015

(51) Int. Cl.
| | |
|---|---|
| F24F 13/00 | (2006.01) |
| B01F 3/04 | (2006.01) |
| A61M 16/16 | (2006.01) |
| A61M 16/10 | (2006.01) |
| F24F 6/00 | (2006.01) |

(52) U.S. Cl.
CPC ............ *A61M 16/162* (2013.01); *A61M 16/109* (2013.01); *B01F 3/04* (2013.01); *F24F 13/00* (2013.01); *F24F 2006/008* (2013.01)

(58) Field of Classification Search
CPC .................................. B01F 3/04; F24F 13/00
USPC ....................... 261/72.1, 119.1, 150
See application file for complete search history.

(56) References Cited

U.S. PATENT DOCUMENTS

| | | | |
|---|---|---|---|
| 4,752,422 A * | 6/1988 | Uchida et al. .................. 261/81 |
| 5,329,939 A | 7/1994 | Howe | |
| 2004/0099967 A1 | 5/2004 | Chen | |
| 2007/0240767 A1 | 10/2007 | Rustad et al. | |
| 2012/0235312 A1 | 9/2012 | Shelly et al. | |
| 2013/0174843 A1 | 7/2013 | Smith et al. | |

FOREIGN PATENT DOCUMENTS

| | | |
|---|---|---|
| GB | 1 448 473 A | 9/1976 |
| TW | M342030 U | 10/2008 |
| TW | I328472 B | 8/2010 |
| WO | WO 2012/123854 A1 | 9/2012 |

\* cited by examiner

*Primary Examiner* — Robert A Hopkins
(74) *Attorney, Agent, or Firm* — Muncy, Geissler, Olds & Lowe, P.C.

(57) ABSTRACT

Disclosed is a liquid container for gas humidification, which comprises a first storage chamber containing a bottom; and a second storage chamber comprising a top wall, a bottom wall and a side wall connected between the top wall and the bottom wall, the second storage chamber being provided with at least one opening which is above the bottom of the first storage chamber, thereby enabling the liquid in the second storage chamber to flow into the first storage chamber in a unidirectional way. In addition, also disclosed is a liquid storage device.

18 Claims, 5 Drawing Sheets

LIQUID CONTAINER FOR GAS HUMIDIFICATION AND LIQUID STORAGE DEVICE

FIELD OF THE INVENTION

This invention relates to a liquid storage device and more particularly to a liquid container for gas humidification to be used with a respiratory aid device.

BACKGROUND OF THE INVENTION

Continuous positive airway pressure (CPAP) therapy has been proven to be an effective treatment for some respiratory conditions, such as obstructive sleep apnea, and there are many types of CPAP devices commercially available for patients.

In order to relieve the discomfort to patients caused by dry respiratory tract during the CPAP therapy, some CPAP devices are equipped with a gas humidifier for humidifying gas to a proper humidity level before delivery to the patients. Typically, a gas humidifier is composed of a liquid container and humidification means, such as a heater or an ultrasonic atomizer. Although a higher capacity of the liquid container increases the amount of liquid accommodated therein for long-time use, such as up to eight hours, a higher initialization power will be required for humidifying more liquid, and it will take more time to achieve a predetermined gas humidity.

One humidifier chamber has been proposed, characterized by using a thermal insulating partition to divide the chamber into a heated reservoir and a supply reservoir, wherein a liquid channel is formed below the partition to allow liquid communication between the two reservoirs.

Also proposed is a pressure support system which has a humidifier containing a holding space, a humidification space and a partition separating the two spaces, an opening being defined on the partition to allow liquid communication between the two spaces.

However, there are still needs to improve conventional designs, particularly to address the problems associated with bi-directional liquid communication.

SUMMARY OF THE INVENTION

It is a primary object of this invention to provide a liquid container for gas humidification which comprises a storage portion and a humidification portion. Liquid in the storage portion is not in direct contact with the humidification means, so the humidification means only humidifies the liquid in the humidification portion. Because the amount of liquid humidified by the humidification means is less than the total amount of liquid in the liquid container, the humidification means may operate at a lower power, a lower initialization power in particular, yet still achieve substantially the same performance. In addition, liquid in the storage portion may be supplied to the humidification portion when the amount of liquid in the humidification portion is less than a certain level, thereby providing the function of automatic liquid supplement.

It is another primary object of this invention to provide a liquid container for gas humidification, which comprises a first storage chamber for holding liquid for gas humidification and a second storage chamber for holding liquid to be supplied to the first storage chamber. A unidirectional, one-way liquid communication is formed between the two chambers, such that when the liquid level in the first storage chamber lowers to a predetermined height, liquid in the second storage chamber will naturally and unidirectionally flow downward into the first storage chamber until the liquid level of the first storage chamber resumes to the predetermined height, thus maintaining a substantially constant liquid amount in the first storage chamber.

It is yet another primary object of this invention to provide a liquid storage device comprising an outer chamber and an inner chamber within the outer chamber. The inner chamber defines therein a supplemental liquid storage space, and a part of the outer chamber defines a storage space for liquid to be heated. When the liquid in the storage space for liquid to be heated is consumed to a certain amount, liquid in the supplemental liquid storage space will enters the storage space for liquid to be heated through an opening formed on the inner chamber.

In order to achieve the above-identified and other objects, this invention discloses a liquid container for gas humidification, comprising: a first storage chamber comprising a bottom; and a second storage chamber comprising a top wall, a bottom wall and a side wall connected between the top wall and the bottom wall, the second storage chamber being provided with at least one opening which is above the bottom of the first storage chamber, thereby enabling liquid in the second storage chamber to flow into the first storage chamber in a unidirectional way, such as downwardly.

Also disclosed herein is a liquid storage device, comprising: an outer chamber defining a receiving space therein; and an inner chamber received in the receiving space, the inner chamber defining a supplemental liquid storage space therein and being provided with at least one opening, wherein a portion of the receiving space not occupied by the inner chamber is divided in respect to the opening into a storage space for liquid to be heated, which is below the opening, and a gas humidification space, which is above the opening.

Further disclosed herein is a liquid storage device, comprising: a first chamber comprising a first reservoir; a second chamber located within the first chamber and comprising a second reservoir; gas passage means for introducing gas out of the second chamber into the second chamber; and liquid passage means for introducing liquid within the second reservoir into the first reservoir, wherein the gas passage means and the liquid passage means can individually be any structure for gas and liquid passage between the chambers, such as an opening, a hole, an orifice, a pipe or a structure equivalent thereto.

It is to be understood that both the foregoing general description and the following detailed description are exemplary and explanatory only and are not restrictive of the invention as defined in the claims.

BRIEF DESCRIPTION OF THE DRAWINGS

A more complete understanding of the subject matter can be derived by referring to the detailed description and claims when considered in conjunction with the following figures, wherein like reference numbers refer to similar elements throughout the figures.

DETAILED DESCRIPTION OF THE INVENTION

Embodiments are illustrated in the accompanying figures to improve understanding of concepts as presented herein. Skilled artisans appreciate that elements in the figures are illustrated for simplicity and clarity and have not necessarily been drawn to scale. For example, the dimensions of some elements in the figures may be exaggerated relative to others to facilitate understanding of the embodiments.

Since various aspects and embodiments are merely exemplary and not limiting, after reading this specification, skilled artisans appreciate that other aspects and embodiments are possible without departing from the scope of the invention. Other features and benefits of any one or more of the embodiments will be apparent from the following detailed description and the claims.

The use of "a" or "an" is employed to describe elements and components described herein. This is done merely for convenience and to give a general sense of the scope of the invention. Accordingly, this description should be read to include one or at least one and the singular also includes the plural unless it is obvious that it is meant otherwise.

As used herein, the terms "comprises," "comprising," "includes," "including," "has," "having" or any other variation thereof are intended to cover a nonexclusive inclusion. For example, a component, structure, article, or apparatus that comprises a list of elements is not necessarily limited to only those elements but may include other elements not expressly listed or inherent to such component, structure, article, or apparatus. Further, unless expressly stated to the contrary, the term "or" refers to an inclusive or and not to an exclusive or. For example, a condition "A or B" is satisfied by any one of the following: A is true (or present) and B is false (or not present), A is false (or not present) and B is true (or present), and both A and B are true (or present).

Figure 1:
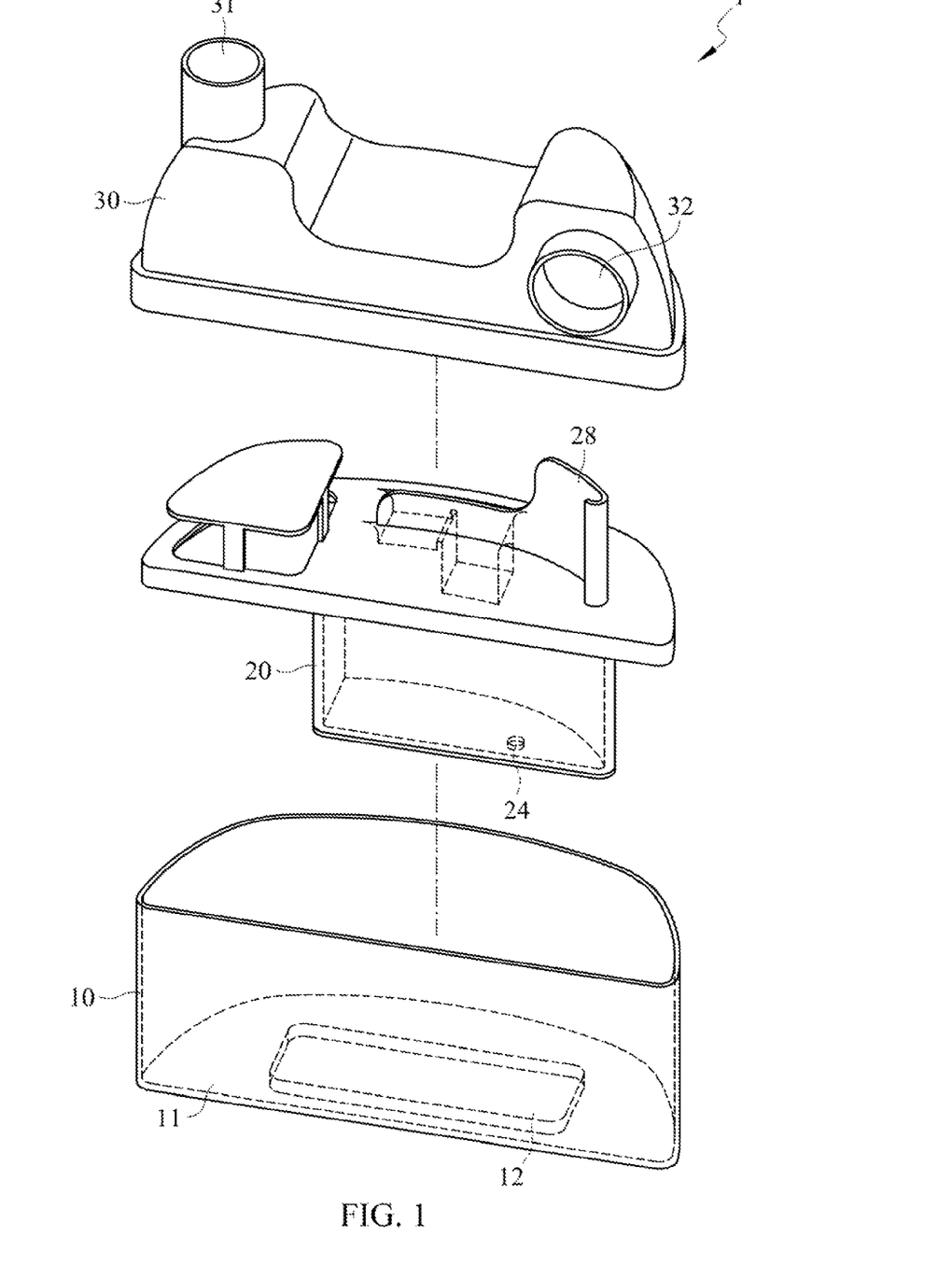
FIG. 1 illustrates an exploded view showing main components of a liquid container for gas humidification according to one embodiment of this invention.

As illustrated in FIG. 1, an exemplary embodiment according to the present disclosure provides a liquid container 1 for humidifying gas and increasing gas humidity, wherein the gas may include air, pure gas or gas mixture, and the humidification may be, without limitation, carried out by heating, evaporation or ultrasonic atomization. The liquid container 1 mainly comprises two chambers, which are the first storage chamber 10 and the second storage chamber 20 disposed for example in the first storage chamber 10. Optionally, as shown in FIG. 1, the liquid container 1 may also include a cover 30 covering the first storage chamber 10 and the second storage chamber 20.

The first storage chamber 10 has a reservoir primarily for holding liquid to be humidified, such as water, normal saline or the like. If humidification is carried out by heating, the liquid to be humidified may be heated and evaporated by a heating board, a heater, a heating plate, or the like installed at a certain position (e.g. heating zone 12) of the bottom 11 of the first storage chamber 10.

The second storage chamber 20 also includes a reservoir primarily for holding supplemental liquid such as water, normal saline or the like. The liquid within the second storage chamber 20 and the first storage chamber 10 may be the same or different. An opening 24 is formed on the second storage chamber 20 such as at the bottom, such that gas is allowed to enter the second storage chamber 20 via the opening 24 and cause air pressure change in the second storage chamber 20, and such that liquid in the second storage chamber 20 may flow downwardly via the opening 24 into the first storage chamber 10 so as to supplement the liquid amount in the first storage chamber 10. In addition, the second storage chamber 20 may be optionally equipped on its surface with an aerodynamic structure 28, such as fins of a certain shape, to regulate the time of gas staying in the liquid container 1 and its movement distance, or to define a path for gas flow, for example.

Moreover, in this embodiment, the liquid container 1 also includes an optional cover 30. The cover 30 may be connected with the first storage chamber 10 to situate the second storage chamber 20 therebetween. In this case, gas entering the gas humidification space of the liquid container 1 via the gas inlet 32 may move along the gas flow path defined by the aerodynamic structure 28 and, after absorbing a certain amount of moisture, leave the gas humidification space of the liquid container 1 via the gas outlet 31, to a user's respiratory tract through a duct for example connected with the gas outlet 31.

As used herein, the term "connect," "connected," "connected to" or "connected with" means "combined, joined, linked or assembled together," and includes direct connection where no intermediate (e.g. a gasket or washer) exists and indirect connection where an intermediate exists between two elements to be connected. In addition, when different components are connected, these components may form an integral, one-piece structure such as by integration in which different components act as different parts of the integral structure, or these components may be distinct and separate components connected together. Unless otherwise specified, means for joining distinct and separate components together includes interlocking, engagement, fastening, mortise and tenon joint, or any other connection means known and understood in the mechanical arts.

Accordingly, depending on the preferences in use and during manufacture, the first storage chamber 10 and the second storage chamber 20 can form an integral structure, or they can be separate and distinct structures assembled together. Similarly, the second storage chamber 20 and the cover 30 can form an integral structure, or they can be separate and distinct structures assembled together.

Figure 2:
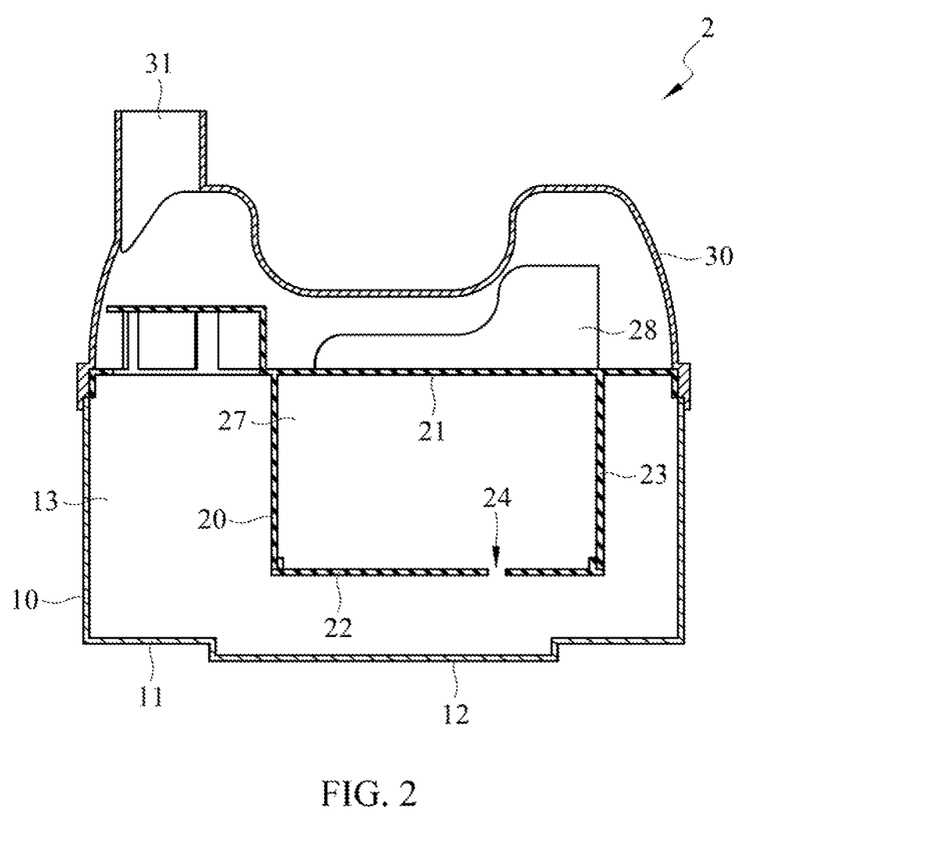
FIG. 2 illustrates a cross-sectional view of a liquid storage device according to one embodiment of this invention.

FIG. 2 illustrates a cross-sectional view of a liquid storage device according to one embodiment of this invention. The liquid storage device 2 mainly comprises a first storage chamber 10, a second storage chamber 20 and a cover 30. As an outer chamber, the first storage chamber 10 defines a receiving space 13 therein, and as an inner chamber, the second storage chamber 20 is disposed within the receiving space 13, wherein the inner chamber defines inwardly a supplemental liquid storage space 27. In this embodiment, the second storage chamber 20 primarily consists of a top wall 21, a bottom wall 22 and a side wall 23 connected therebetween, preferably in an airtight manner. For example, the bottom wall 22 and side wall 23 of the second storage chamber 20 may form a unitary and integral structure, and the top wall 21 of the second storage chamber 20 may be removably covered on the side wall 23, such that the space defined collectively by the top wall 21, the bottom wall 22 and the side wall 23 is airtight with respect to and not in gas communication with the exterior except through the opening 24, as described below.

To form gas communication and liquid communication between the first storage chamber 10 and the second storage chamber 20, the second storage chamber 20 is provided with at least one opening 24 for example on the bottom wall 22, such that gas can enter the second storage chamber 20 and liquid can leave the supplemental liquid storage space 27 of the second storage chamber 20. As illustrated in FIG. 2, the position of the opening 24 is above the bottom 11 of the first storage chamber 10, so liquid from the second storage chamber 20 will be driven naturally to flow downwardly into the first storage chamber 10.

In this exemplary embodiment, there is only one opening 24 formed on the bottom wall 22 of the second storage chamber 20, so gas and liquid respectively enter and leave the space defined within the second storage chamber 20 via the same opening 24. In order to serve the dual purpose of gas entry and liquid exit, parameters of the opening 24 such as aperture size, shape and the so on can be designed without undue experimentation, such as in view of the cohesion force within liquid in the second storage chamber 20, hydraulic pressure, air pressure and the like. A circular opening may be used, for example, which has an aperture diameter ranging from 0.5 mm to 5 mm, but not limited thereto.

In order to further explain the concepts and principles behind this invention, the operational states of various embodiments with the presence of liquid are described with the accompanying drawings. However, there is no intention to be bound by any expressed or implied theory presented in the preceding technical field, background, brief summary or the following detailed description.

Figure 3:
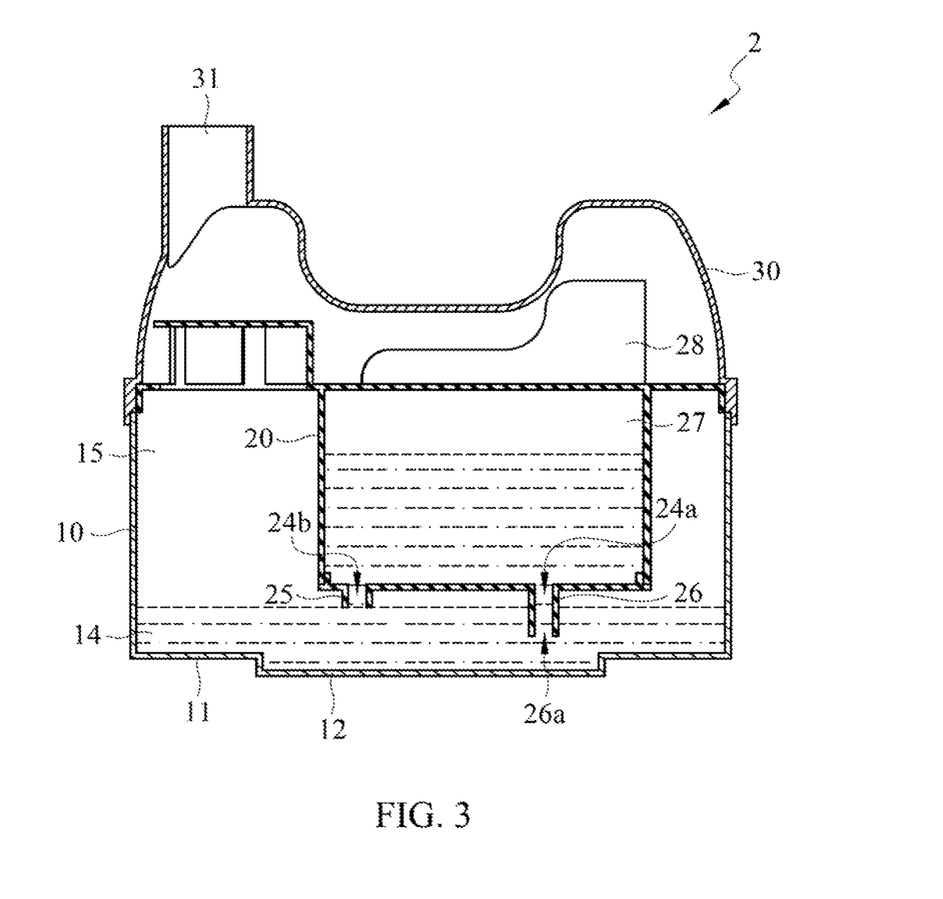
FIGS. 3 and 4 illustrate cross-sectional views of a liquid storage device according to one embodiment of this invention in operational states with the presence of liquid.

FIG. 3 illustrates a cross-sectional view of an exemplary liquid storage device for gas humidification in an operational state. When in use, the second storage chamber 20 of the liquid storage device 2 can first be filled with liquid. The filling process may involve separating the top wall of the second storage chamber 20 from the side wall, filling the liquid into the supplemental liquid storage space 27, and then joining or connecting the top wall and the side wall in an airtight manner. Alternatively, a switchable liquid injection port may be formed on any desirable portion of the second storage chamber 20 for liquid injection, and after being filled with the liquid, the second storage chamber 20 may then be assembled between the cover 30 and the first storage chamber 10. Further alternatively, the second storage chamber 20 may be made as a disposable component, and the supplemental liquid storage space 27 is filled with the liquid in advance during production and then sealed airtight, such that the second storage chamber 20 can be mounted by users without the additional liquid loading process. For example, the second storage chamber 20 may be placed into the receiving space of the first storage chamber 10, allowing liquid to flow into the first storage chamber 10 through the opening on the second storage chamber 20. Depending on the user's need, a predetermined amount of liquid may be loaded into the first storage chamber 10 before setting the second storage chamber 20.

In this embodiment, two openings 24a and 24b are formed on the bottom of the second storage chamber 20. A liquid flow pipe 26 is formed extending from the openings 24a downwardly, and the terminal orifice 26a of the liquid flow pipe 26 is above the bottom 11 of the first storage chamber 10. In addition, a gas flow pipe 25 is formed extending from the openings 24b downwardly. Two openings are used in this embodiment for allowing liquid to move from the second storage chamber 20 into the first storage chamber 10 and allowing gas to move from the first storage chamber 10 into the second storage chamber 20. However, the liquid or gas is not limited to entering or exiting through a specific opening. In word words, when two or more openings are formed, each opening may serve for gas and/or liquid passage. In view of several factors including aperture size, opening shape, cohesion force within liquid, hydraulic pressure, air pressure and the like, different openings may be designed either with more tendency toward allowing gas to enter the second storage chamber 20 or with more tendency toward allowing liquid to leave the second storage chamber 20, and the size or shape of different openings may be the same or different. In this embodiment, for example, the openings 24a and 24b may individually have an aperture diameter from 0.5 mm to 5 mm, but not limited thereto.

As shown in FIG. 3, the two openings are both extended downwardly to form the gas flow pipe 25 and the liquid flow pipe 26 respectively, and the length, the pipe diameter, and other parameters of the two pipes may be the same or different. For example, the length of the liquid flow pipe 26 may be greater than that of the gas flow pipe 25. In a situation where a plurality of pipes of different lengths are formed, the longer pipe sustains a greater pressure at the bottom end, so liquid has a greater tendency to flow from the longer pipe. In other words, a longer pipe, such as the liquid flow pipe 26 in this embodiment, is more suitable for discharging liquid from the second storage chamber 20. However, as stated above, the liquid flow pipe 26 is not limited to serve as a passage for liquid discharge only but may also be useful for gas entry in some circumstances, and, similarly, the gas flow pipe 25 is not limited to serve as a passage for gas entry only but may also be useful for liquid discharge in some circumstances, both depending on various environmental parameters in operational states and the structural design of the second storage chamber 20. In this embodiment, for example, the length of the gas flow pipe 25 extending downwardly may be less than 10 mm, and the liquid flow pipe 26 may be 5 mm longer than the gas flow pipe 25, such as less than 15 mm, but not limited thereto.

In an operational state, gas primarily enters the second storage chamber 20 through the gas flow pipe 25, and liquid primarily enters the first storage chamber 10 from the supplemental liquid storage space 27 through the liquid flow pipe 26, such that the liquid level in the first storage chamber 10 gradually raises and that the liquid level in the supplemental liquid storage space 27 gradually lowers at the same time. When the liquid level in the first storage chamber 10 raises to the position of the orifice at the bottom of the gas flow pipe 25, before which the terminal orifice 26a of the liquid flow pipe 26 has been submerged by the liquid, the gas flow pipe 25 is sealed by the liquid, and gas is prevented from entering the second storage chamber 20 via the gas flow pipe 25 and causing pressure change, thus achieving a substantially balanced or steady state of the system within the liquid storage device 2. Accordingly, in an embodiment where a plurality of openings are employed, the position or height of the opening(s) primarily for gas entry can determine the liquid level in the first storage chamber 10 under the steady state, during which the space within the first storage chamber 10 is divided into two parts—the space below the opening forming a storage space for liquid to be heated (i.e. the space occupied by the liquid, as indicated by the numeral 14 in FIG. 3), and the space above the opening forming a gas humidification space (i.e. the space occupied by the gas, as indicated by the numeral 15 in FIG. 3).

Figure 4:
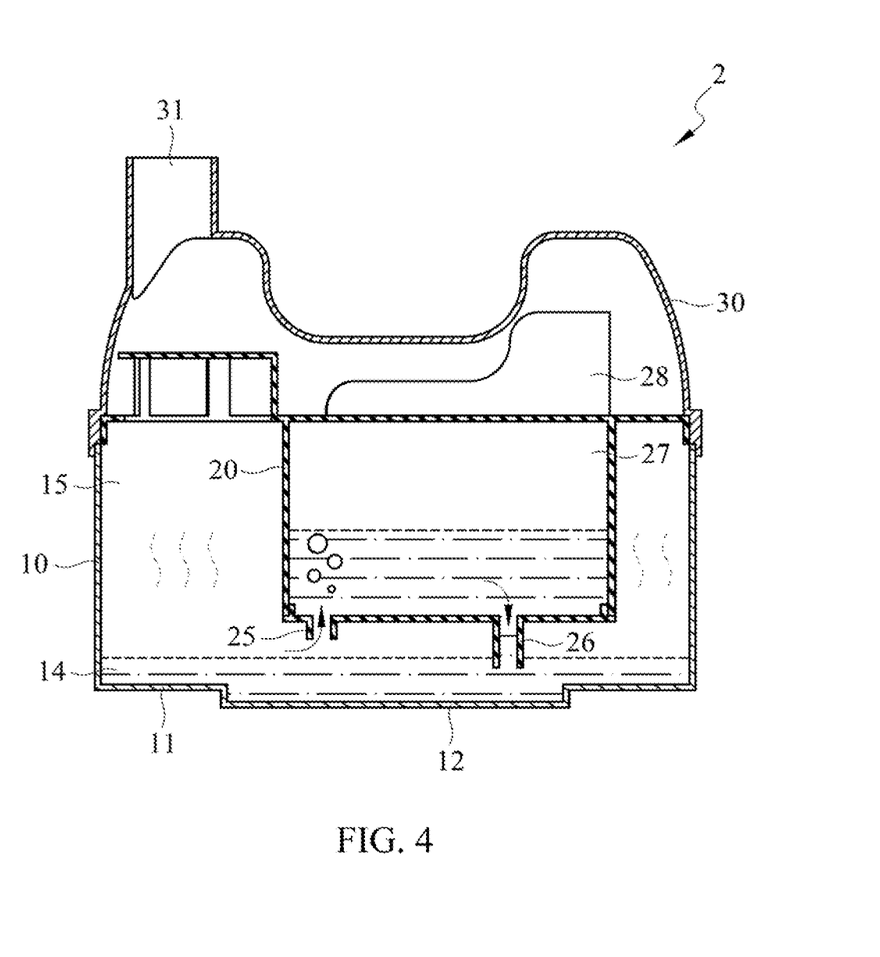

During operation of a humidifier such as a heater or an atomizer, as shown in FIG. 4, liquid in the storage space for liquid to be heated 14 will be evaporated or atomized and then be absorbed by the gas in the gas humidification space 15, which then leaves the liquid storage device 2 from the gas outlet 31. Thus, during operation, the liquid level in the first storage chamber 10 will gradually lower, and when the gas flow pipe 25 is no longer sealed by the liquid, gas may reenter the second storage chamber 20 via the gas flow pipe 25 and cause air pressure change in the second storage chamber 20 (i.e. air pressure increases due to the increasing gas amount), such that liquid may be driven to flow downwardly and leave the supplemental liquid storage space 27 via the liquid flow pipe 26, achieving the purpose of automatic supplement of liquid to the storage space for liquid to be heated 14. Subsequently, the liquid level gradually raises again in the storage space for liquid to be heated 14, and the gas flow pipe 25 is sealed by the raising liquid level to block the gas entry into the second storage chamber 20 therefrom, thereby reaching the steady state mentioned above as illustrated in FIG. 3. Therefore, when in use, the design of this embodiment can maintain a substantially constant amount of liquid in the first storage chamber 10.

While various stages during operation are described according to their temporal sequence, however, it is understood that, when in actual use, different stages may happen one after the other or almost at the same time. Therefore, during operation, the liquid storage device 2 is substantially maintained at a dynamic equilibrium or steady state until all the liquid in the supplemental liquid storage space 27 is used up.

Figure 5:
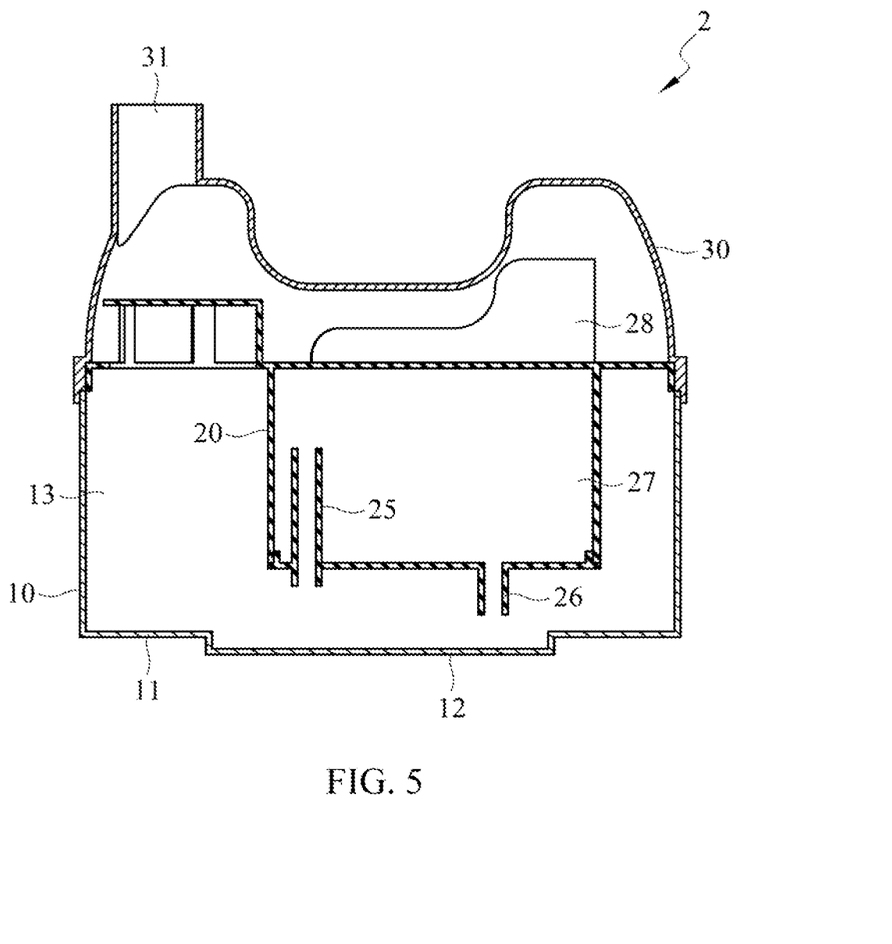
FIG. 5 illustrates a cross-sectional view of a liquid storage device according to another embodiment of this invention.

FIG. 5 illustrates a cross-sectional view of a liquid storage device 2 according to another embodiment of this invention, in which the opening primarily for gas passage is penetrated by the gas flow pipe 25. The operational principle behind this embodiment is substantially the same as other embodiments. When the bottom opening of the gas flow pipe 25 is not sealed for example by liquid, gas enters the second storage chamber 20 via the gas flow pipe 25, and liquid in the supplemental liquid storage space 27 flows into the first storage chamber 10 through the liquid flow pipe 26. When the liquid level in the first storage chamber 10 raises to a predetermined degree, such as sealing the bottom opening of the gas flow pipe 25, gas is prevented from entering the second storage chamber 20 and inducing air pressure increase therein, and liquid flow is inhibited from the supplemental liquid storage space 27 into the first storage chamber 10. In addition, when the liquid level in the first storage chamber 10 lowers during gas humidification, gas can be allowed to enter the second storage chamber 20 via the gas flow pipe 25 again, and liquid is similarly allowed to flow from the supplemental liquid storage space 27 into the first storage chamber 10 again.

The present embodiment is characterized in that the gas flow pipe 25 penetrates into the second storage chamber 20 and that the top opening thereof is above the liquid level in the second storage chamber 20, such that the gas flow pipe 25 contains substantially no liquid therein. Thus, when entering the second storage chamber 20 via the gas flow pipe 25, gas will not contact with liquid and will not form bubbles as shown in FIG. 4, thereby reducing the voice or noise from the operating liquid storage device 2 caused by bursting bubbles, and making this embodiment particularly suitable for a situation which requires less noise, such as when a user is sleeping.

As mentioned above, in this invention, different components or structures may be formed as one piece or individually and separately formed and then assembled together. For example, suitable molds may be used to make any part of the liquid container or the liquid storage device, such as using extrusion molding, injection molding or other molding processes known to a person skilled in the art. Furthermore, the liquid container or the liquid storage device of this invention may be made of various materials, such different plastic materials, or materials commonly used for medical grade products.

The above detailed description is merely illustrative in nature and is not intended to limit the embodiments of the subject matter or the application and uses of such embodiments. As used herein, the term "exemplary" means "serving as an example, instance, or illustration." Any implementation described herein as exemplary is not necessarily to be construed as preferred or advantageous over other implementations.

Moreover, while at least one exemplary embodiment has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, various changes can be made in the function and arrangement of elements without departing from the scope defined by the claims, which include known equivalents and foreseeable equivalents at the time of filing this patent application.

What is claimed is:

1. A liquid container for gas humidification, comprising:
a first storage chamber comprising a bottom; and
a second storage chamber comprising a top wall, a bottom wall and a side wall connected between the top wall and the bottom wall, the second storage chamber being provided with at least one opening which is above the bottom of the first storage chamber, thereby enabling liquid in the second storage chamber to flow into the first storage chamber in a unidirectional way, wherein the opening is a gas flow opening, and the bottom wall is further provided with a liquid flow opening.

2. The liquid container for gas humidification of claim 1, wherein the gas flow opening is formed on the bottom wall.

3. The liquid container for gas humidification of claim 1, wherein a pipe is formed extending outwardly from at least one of the gas flow opening and the liquid flow opening.

4. The liquid container for gas humidification of claim 1, wherein the gas flow opening is penetrated by a gas flow pipe.

5. The liquid container for gas humidification of claim 1, wherein a liquid flow pipe is formed extending outwardly from the liquid flow opening, and a terminal orifice of the liquid flow pipe is above the bottom of the first storage chamber.

6. The liquid container for gas humidification of claim 1, wherein the side wall is airtightly connected with the top wall and the bottom wall.

7. The liquid container for gas humidification of claim 1, further comprising a cover connected with the first storage chamber and having a gas outlet.

8. The liquid container for gas humidification of claim 7, wherein the second storage chamber is connected with the cover and received between the cover and the first storage chamber.

9. The liquid container for gas humidification of claim 7, wherein the second storage chamber is integrally formed with the cover.

10. The liquid container for gas humidification of claim 1, wherein the bottom of the first storage chamber at least partially defines a heating zone.

11. The liquid container for gas humidification of claim 7, wherein the second storage chamber is integrally formed with the cover.

12. A liquid storage device, comprising:
an outer chamber defining a receiving space therein; and
an inner chamber received in the receiving space, the inner chamber defining a supplemental liquid storage space therein and being provided with at least one opening,
wherein a portion of the receiving space not occupied by the inner chamber is divided in respect to the opening into a storage space for liquid to be heated, which is below the opening, and a gas humidification space, which is above the opening.

13. The liquid storage device of claim 12, wherein the opening is a gas flow opening, and the inner chamber is further provided with a liquid flow opening.

14. The liquid storage device of claim 13, wherein the gas flow opening and the liquid flow opening are individually surrounded by a pipe.

15. The liquid storage device of claim 12, further comprising:
a cover connected with the outer chamber;
a gas inlet allowing introduction of gas into the gas humidification space; and
a gas outlet through which the gas can escape from the gas humidification space after being humidified.

16. A liquid storage device, comprising:
a first chamber comprising a first reservoir;
a second chamber located within the first chamber and comprising a second reservoir;
means for introducing gas into the second chamber; and
means for introducing liquid within the second reservoir into the first reservoir.

17. A liquid container for gas humidification, comprising:
a first storage chamber comprising a bottom;
a second storage chamber comprising a top wall, a bottom wall and a side wall connected between the top wall and the bottom wall, the second storage chamber being provided with at least one opening which is above the bottom of the first storage chamber, thereby enabling liquid in the second storage chamber to flow into the first storage chamber; and
a cover connected with the first storage chamber and having a gas outlet.

18. The liquid container for gas humidification of claim 17, wherein the second storage chamber is connected with the cover and received between the cover and the first storage chamber.

* * * * *